US008529617B2

(12) United States Patent
Lambert et al.

(10) Patent No.: US 8,529,617 B2
(45) Date of Patent: *Sep. 10, 2013

(54) STENTS INCLUDING POLY(L-LACTIDE) FORMULATIONS THAT MINIMIZE MOLECULAR WEIGHT DROP DURING PROCESSING

(75) Inventors: Byron Lambert, Temecula, CA (US); Yunbing Wang, Sunnyvale, CA (US); James Oberhauser, Saratoga, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/481,523

(22) Filed: May 25, 2012

(65) Prior Publication Data

US 2012/0239135 A1 Sep. 20, 2012

Related U.S. Application Data

(63) Continuation of application No. 12/559,402, filed on Sep. 14, 2009, now Pat. No. 8,207,240.

(51) Int. Cl.
*A61F 2/06* (2013.01)
(52) U.S. Cl.
USPC ........................................ 623/1.15; 623/1.22
(58) Field of Classification Search
USPC ............... 623/1.38, 1.49–1.54, 1.15–1.22
See application file for complete search history.

(56) References Cited

U.S. PATENT DOCUMENTS

| 6,469,133 | B2 * | 10/2002 | Baker et al. ................... 528/354 |
| 6,762,418 | B2 | 7/2004 | Lambert et al. |
| 7,959,857 | B2 * | 6/2011 | Freeman et al. ............... 422/22 |
| 8,034,287 | B2 * | 10/2011 | Freeman et al. ............... 422/22 |
| 8,147,744 | B2 * | 4/2012 | Kleiner ......................... 264/459 |
| 8,182,890 | B2 * | 5/2012 | Zheng et al. .................. 428/36.9 |
| 8,207,240 | B2 * | 6/2012 | Lambert et al. ................ 522/74 |
| 2007/0280851 | A1 | 12/2007 | Freeman et al. |
| 2008/0010947 | A1 | 1/2008 | Huang et al. |
| 2008/0039545 | A1 | 2/2008 | Muratoglu et al. |
| 2008/0299002 | A1 * | 12/2008 | Freeman et al. ............... 422/22 |
| 2009/0074610 | A1 | 3/2009 | Sabaria |
| 2009/0182415 | A1 * | 7/2009 | Wang .......................... 623/1.49 |
| 2009/0259297 | A1 * | 10/2009 | Wang .......................... 623/1.34 |
| 2010/0198330 | A1 | 8/2010 | Hossainy et al. |
| 2010/0262223 | A1 * | 10/2010 | Kleiner ........................ 623/1.15 |
| 2010/0262224 | A1 * | 10/2010 | Kleiner ........................ 623/1.15 |
| 2011/0066223 | A1 * | 3/2011 | Hossainy et al. ............. 623/1.15 |
| 2012/0149850 | A1 * | 6/2012 | Kleiner ........................ 525/419 |
| 2012/0150283 | A1 * | 6/2012 | Kleiner ........................ 623/1.38 |

OTHER PUBLICATIONS

U.S. Appl. No. 12/364,321, filed Feb. 2, 2009, Wang.
ABSORB: Bioabsorbable Coronary Stents Successfully and Safely Deployed, downloaded from: www.tct2006.com/Dailies_TCT2006, Nov. 14, 2008, 1 pg.
Compression Test, Materials Testing Solutions, downloaded from: www.instron.us/wa/applications/test_types/compressions.aspx, Nov. 14, 2008, 1 pg.
Costa et al., "Angiographic Results of the First Human Experience with Everolimus-Eluting Stents for the Treatment of Coronary Lesions (the Future I Trial)", The Am. J. of Card. vol. 95, pp. 113-116 (2005).
Fajadet et al., "Randomized, Double-Blind, Multicenter Study of the Endeavor Zotarolimus-Eluting Phosphorylcholine-Encapsulated Stent for Treatment of Native Coronary Artey Lessions", Circulation, pp. 798-806 (2006).
Grube et al., "Six-and Twelve-Month Results from First Human Experience Using Everolimus-Eluting Stents with Bioabsorbable Polymer", Circulation, pp. 2168-2171 (2004).
Gussenhoven et al., "Intravascular Ultrasonic Imaging: Histologic and Echographic Correlation", Eur. Vasc. Surg. 3, pp. 571-576 (1989).
Kukreja et al., "Biodegradable drug eluting stents: invasive and non-invasive imaging", Euro Intervention 2, p. 403 (2006).
Lachowitzer "Assessing Radial Tests for Endovascular Implants", Medical Device Link, downloaded from: www.devicelink.com/grabber.php3?, Nov. 10, 2008, 4 pgs.
Markman, "Absorbable coronary stents", Lancet 369, pp. 1839-1840 (2007).
Meredith et al., "First-in-human study of the Endeavor ABT-578-eluting phosphorylcholine-encapsulated stent system in de novo native coronary artery lesions: endeavor I Trial", Clinical Research, EuroInterv. 1; pp. 157-164 (2005).
Mintz et al., "Arterial Remodeling after Coronary Angioplasty: A Serial Intravascular Ultrasound Study", Circulation 94, pp. 35-43 (1996).
Ormiston et al., "A bioabsorbable everolimus-eluting coronary stent system for patients with single de-novo coronary artery lesions (ABSORB): a prospective open-label trial", Lancet 371, pp. 899-907 (2008).
Ormiston et al., "First-in-Human Impantation of a Fully Bioabsorbable Drug-Eluting Stent: The BVS Poly-L-Lactic Acid Everolimus-Eluting Coronary Stent", Catheterization and Cardiovascular Interventions 69: pp. 128-131 (2007).
Pietrzak et al., "Bioabsorbable Polymer Science for the Practicing Surgeon", The J. of Craniofacial Surgery vol. 8, No. 2, pp. 87-91 (1997).
Radial testing of Vascular Stents (ASTM F2079 and ASTM F2477), Materials Testing Solutions, downloaded from: www.instron.us/wa/solutions//Stents.aspx, Nov. 14, 2008, 1 pg.

(Continued)

*Primary Examiner* — Nathan M Nutter
(74) *Attorney, Agent, or Firm* — Squire Sanders (US) LLP

(57) ABSTRACT

A stent scaffolding including a polymer formulation comprising PLLA and polymandelide is disclosed. The polymandelide reduces the molecular weight drop during processing, particularly during sterilization. The stent scaffolding can further include one or more additional stabilizing agents that additionally reduce the molecular weight drop during processing.

27 Claims, 1 Drawing Sheet

(56) References Cited

OTHER PUBLICATIONS

Ramcharitar et al., "Fully Biodegradable Coronary Stents: Progress to Date", Am. J. of Card. Drugs vol. 8, No. 5, pp. 305-314 (2008) Abstract 2 pgs.

Serruys et al., "A bioabsorbable everolimus-eluting coronary stent system (ABSORB): 2-year outcomes and results from multiple imaging methods", Lancet 373, pp. 897-910 (2009).

Slottow et al., "Optical coherence tomography and intravascular ultrasound imaging of bioabsorbable magnesium stent degradation in porcine coronary arteries", Cardiovasc. Revascularization Medicine 9, pp. 248-254 (2008).

Stone et al., "A Polymer-Based, Paclitaxel-Elluting Stent in Patients with Coronary Artery Disease", The New England J. of Medicine, 350; 3, pp. 221-231 (2004).

Tanimoto et al., "Comparison of in Vivo Acute Stent Recoil Between the Bioabsorbable Everolimus-Eluting Coronary Stent and the Everolimus-Eluting Cobalt Chromium Coronary Stent: Insights From the ABSORB and Spirit Trails", Catheterization and Cardiovascular Interventions 70, pp. 515-523 (2007).

Tanimoto et al., "Late Stent Recoil of the Bioabsorbable Everolimus-Eluting Coronary Stent and its Relationship with Plaque Morphology", J. of Am. Col. of Cardiology vol. 52, No. 20, pp. 1616-1620 (2008).

Wood "ABSORBing the Details: 12-Month Results for Bioabsorbable, Everolimus-Eluting Stent", downloaded from: www.medscape.com/viewarticle/571705, Nov. 14, 2008, 16 pgs.

Liu et al., "Synthesis of Polymandelide: A Degradable Polylactide Derivative with Polystyrene-like Properties", Macromolecules 40(17), pp. 6040-6047 (2007) Abstract 1 pg.

Mitomo et al., "Improvement of heat stability of poly(L-lactic acid) by radiation-induced crosslinking", Polymer 46, pp. 4695-4703 (2005).

\* cited by examiner

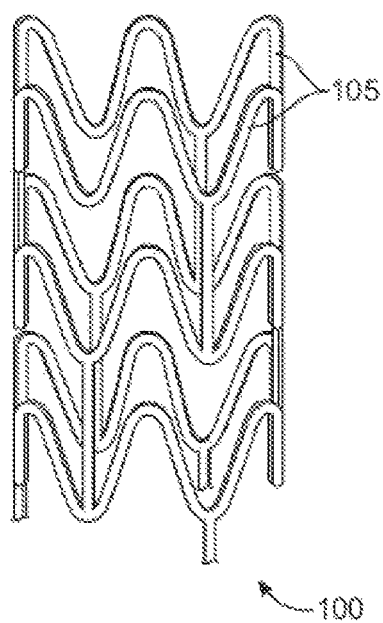
PRIOR ART

STENTS INCLUDING POLY(L-LACTIDE) FORMULATIONS THAT MINIMIZE MOLECULAR WEIGHT DROP DURING PROCESSING

CROSS-REFERENCE TO RELATED APPLICATION

This application is a continuation of U.S. patent application Ser. No. 12/559,402, now U.S. Pat. No. 8,207,240, filed Sep. 14, 2009, the entire disclosure is incorporated herein by reference.

BACKGROUND OF THE INVENTION

1. Field of the Invention

This invention relates to implantable medical devices, such as stents, with improved thermal and radiation stability and methods of sterilizing the stents.

2. Description of the State of the Art

This invention relates to various kinds of implantable medical devices including structures made from polymers. Such implantable medical devices include, but are not limited to, radially expandable prostheses, such as stents and stent grafts, catheters, and pacemaker leads.

Radially expandable endoprostheses are adapted to be implanted in a bodily lumen. An "endoprosthesis" refers to an artificial device that is placed inside the body. A "lumen" refers to a cavity of a tubular organ such as a blood vessel. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment.

"Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a constraining member such as a retractable sheath or a sock. When the stent is in a desired bodily location, the sheath may be withdrawn which allows the stent to self-expand.

The stent must be able to satisfy a number of requirements such as the radial strength necessary to withstand the structural loads, namely radial compressive forces, imposed on the stent as it supports the walls of a vessel. Once expanded, the stent must adequately maintain its size and shape throughout its service life despite the various forces that may come to bear on it, including the cyclic loading induced by the beating heart. For example, a radially directed force may tend to cause a stent to recoil inward. In addition, the stent must possess sufficient flexibility to allow for crimping, expansion, and cyclic loading. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment).

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for implantable medical devices, such as stents, to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable bioabsorbable polymers can be configured to partially or completely erode away after the clinical need for them has ended.

SUMMARY OF THE INVENTION

Embodiments of the present invention include a stent comprising a stent scaffolding, the stent scaffolding including a polymer formulation including poly(L-lactide) and polymandelide.

Embodiments of the present invention include a stent comprising a stent scaffolding, the stent scaffolding comprising: a polymer formulation including poly(L-lactide) and polymandelide; and one or more stabilizing agents incorporated in the scaffolding, wherein the one or more stabilizing agents reduce the molecular weight reduction of the poly(L-lactide) upon its exposure to radiation, wherein the stabilizing agents are selected from the group consisting of a free radical scavenger, an oxygen scavenger, and a dessicant.

Embodiments of the present invention include a medical device system comprising: a sealed package; a stent scaffolding disposed within the sealed package, wherein the scaffolding comprises a polymer formulation including poly(L-lactide) and polymandelide; and one or more stabilizing agents within the sealed package, wherein the one or more stabilizing agents reduce the molecular weight reduction of the poly (L-lactide) upon its exposure to radiation, wherein the stabilizing agents are selected from the group consisting of a free radical scavenger, an oxygen scavenger, and a dessicant.

BRIEF DESCRIPTION OF THE DRAWINGS

FIG. 1 depicts a stent.

DETAILED DESCRIPTION OF THE INVENTION

The methods and devices described herein are generally applicable to any implantable medical device. In particular, the methods can be applied to tubular implantable medical devices such as self-expandable stents, balloon-expandable stents, stent-grafts, and pacemaker leads. The embodiments are particularly relevant, for reasons discussed below, to implantable medical devices, such as stents, having a polymeric substrate, body, or scaffolding. As described in more detail below, the stents of the present invention include a body that can be a scaffolding that is designed to expand and provide patency to a narrowed portion of blood vessel. The body or scaffolding can be made in part or entirely out of the polymer formulation.

An exemplary structure of a stent is shown in FIG. 1. FIG. 1 depicts a stent 100 which is made up of struts 105. The embodiments disclosed herein are not limited to fabricating stents or to the stent pattern illustrated in FIG. 1. The embodiments are easily applicable to other stent patterns and other devices. The variations in the structure of patterns are virtually unlimited. A stent such as stent 100 may be fabricated from a tube by forming a pattern in the tube with a technique such as laser cutting or chemical etching.

Furthermore, stents and other implantable medical devices have been designed for the localized delivery of a therapeutic agent. A medicated stent may be constructed by coating the device or substrate with a coating material containing a therapeutic agent. The body or scaffolding of the device may also contain a therapeutic agent.

Embodiments of the present invention relate generally to stents and methods of processing such stents that have a body or scaffolding made from a polymer formulation that includes poly(L-lactide) (PLLA) and a stabilizer polymer (polymandelide) or PLLA chemically modified with polymandelide. The polymer formulation can also include poly(L-lactide-co-glycolide) (PLGA) and polymandelide or PLGA chemically modified with polymandelide. This polymer formulation has improved radiation and thermal stability over a PLLA or PLGA that contain no stabilizer polymer or agents. In particular, the polymer formulation has lower molecular weight degradation or reduction when exposed to radiation and high temperature melt processing than PLLA or PLGA. The PLGA used can include any molar ratio of L-lactide (LLA) to glycolide (GA). In particular, the PLGA can have a molar ratio of (LA:GA) including 85:15 (or a range of 82:18 to 88:12), 95:5 (or a range of 93:7 to 97:3), or commercially available PLGA products identified as having these molar ratios.

"Molecular weight" refers to any of the conventional measures of molecular weight for polymers such as number average molecular weight (Mn), weight average molecular weight (Mw), and inherent viscosity.

The molecular weight at implantation of a polymeric stent body or scaffolding is a critical parameter that influences the performance of the stent in the treatment of blood vessel. The temporal profiles of the mechanical properties (e.g., radial strength), mechanical integrity, and mass loss are important features of stent performance which are influenced by the starting molecular weight. In particular, the stent scaffolding should have sufficient radial strength to provide patency for at least about one month. In addition, the scaffolding of the stent should erode away completely in about eighteen months to two years. Due to these and other performance requirements of a stent, there is a minimum range of molecular weight for a finished product that is ready for storage, shipping, and implantation.

A polymer, such as a biodegradable polyester (e.g., PLLA or PLGA), generally is susceptible to molecular weight degradation (a decrease in molecular weight) from exposure to heat, light and other types of radiation (electron beam, gamma rays, etc.), oxygen, and moisture. As mentioned above, some processing steps in fabrication of polymer stents cause molecular weight reduction. The most significant molecular weight reduction occurs during formation of the stent precursor (which involves melt processing) and from radiation sterilization of the stent.

A PLLA stent precursor is formed by feeding PLLA resin to the extruder followed by forming a tube from the extruded resin. In extrusion, a polymer melt is conveyed through an extruder barrel to an exit port. The polymer is fed to an extruder barrel near its proximal end in a solid form, for example, as a pellet from a hopper. The polymer in the extruder barrel is heated to temperatures near or above the melting temperature (Tm) of the polymer. The polymer melt exits the distal end of the extruder barrel into a die. The die imparts a cylindrical shape to the polymer melt exiting the die, which is cooled to form a tube. PLLA has a melting temperature between 173-178° C. (Medical Plastics and Biomaterials Magazine, March 1998) and can be extruded at a temperature of at least about 180° C., 180-210° C., 210-220° C., or greater than 220° C.

Prior to laser machining a stent pattern in the tube, the polymer tube stent precursor can be radially expanded to increase the radial strength of the tube and the finished stent. The polymer tube can be radially expanded using a blow molding process. In the blow molding process, the polymer tube is heated to a temperature above a glass transition temperature (Tg) of the polymer, but less than the Tm of the polymer. For example, a PLLA tube can be heated to a temperature during blow molding to a temperature between 65-120° C.

A stent scaffolding can then be formed from the polymer tube, for example, by laser machining a pattern into the tube. The stent scaffolding can also be coated with a therapeutic coating prior to crimping the stent onto a catheter. The stent and catheter are typically sealed in a pouch for sterilization, storage and shipping. Both the radial expansion and laser machining steps can result in molecular weight reduction.

For sterilization, the stent is sealed in the pouch filled with an inert gas such as argon or nitrogen. The relative humidity may be about 10% and oxygen content of about 0.03%. During e-beam sterilization (e.g., 20-30 kGy), for example, free radicals would be produced. Furthermore, the formed free radicals attack the polymer chain and cause more chain scission, which causes significant polymer molecular weight drop (about 50% drop in Mw at 25 kGy) during sterilization. Chain scission is enhanced by the existence of oxygen and moisture in the package during irradiation.

The packaged stent and catheter are sterilized to reduce the bioburden of the stent and delivery system to a specified level. Bioburden refers generally to the number of microorganisms with which an object is contaminated. The degree of sterilization is typically measured by a sterility assurance level (SAL) which refers to the probability of a viable microorganism being present on a product unit after sterilization. The required SAL for a product is dependent on the intended use of the product. For example, a product, such as a stent, to be used in the body's fluid path is considered a Class III device and requires an SAL of $10^{-6}$. SAL's for various medical devices can be found in materials from the Association for the Advancement of Medical Instrumentation (AAMI) in Arlington, Va.

The sterilization can be performed by exposing the stent and catheter to radiation, for example, electron beam (e-beam), gamma ray, and x-ray sterilization. A sterilization dose can be determined by selecting a dose that provides a required SAL. A sample can be exposed to the required dose in one or multiple passes.

In general, molecular weight of the polymer decreases due to chemical reactions within a polymer chain, between polymer chains and other species, and between polymer chains. The chemical degradation of polymers can arise from several different chemical reaction mechanisms. In one mechanism, moisture can react with polymer chains by hydrolysis, resulting in chain scission and a reduction in molecular weight. In other mechanisms, heat, light and other types of radiation cause chain scission by free radical reactions and non-free radical reactions. Oxygen can accelerate and propagate the free radical reactions. Free radical formation results in chain scission, resulting in the formation of a series of byproducts, such as monomers (e.g., lactide monomers from PLLA), cyclic oligomers, and shorter polymer chains.

PLLA, for example, typically has at least one hydroxyl end group and has the general formula: R—[OCH(CH3)CO]n-OH, which will be abbreviated as: PLLA-OH. Poly(L-lactide) is subject to thermal degradation at elevated temperatures, with significant degradation (measured as weight loss) starting at about 200° C. and increasing at higher temperatures. The polymer is subject to molecular weight degradation by both free radical and non-free radical mechanisms that result in random chain scission which generates by-products such as shorter chains and oligomers with new end groups. The extrusion process results in a decrease in molecular weight, for example, of up to 20%, 20%-40%, or greater than 40% of the initial Mn or Mw.

Radiation sterilization using high-energy radiation, such as electron beams (e-beam), gamma and x-ray radiation, tends to produce ionization and excitation in polymer molecules. These energy-rich species undergo dissociation, subtraction, and addition reactions in a sequence leading to chemical degradation. The degradation can occur during, immediately after, or even days, weeks, or months after exposure to radiation which often results in physical and chemical cross-linking or chain scission. Resultant physical changes can include embrittlement, discoloration, odor generation, stiffening, and softening, among others.

In particular, the deterioration of the performance of polymers due to e-beam radiation sterilization has been associated with free radical formation during radiation exposure and by scission of the polymer chains. The reaction is dependent on e-beam dose and temperature.

Polymer molecular weight may significantly decrease during the processing steps of stent manufacture. An example is fabrication of a stent having a PLLA stent scaffolding without polymandelide or other stabilizing agents in which the Mw decreases from about 550 kg/mol (PLLA resin) to about 160 kg/mol after sterilization, about a 70% drop in Mw. Extrusion of the polymer tube can result in a decrease to about 380 kg/mol from the initial 550 kg/mol, about a 31% drop in Mw. The molecular weight slightly decreased to about 340 kg/mol after radial expansion and laser cutting, about a 10% drop in Mw. After sterilization by electron beam irradiation (in the range of 20-30 kGy with average dose at 25 kGy), the Mw is about 160 kg/mol, about a 53% drop in Mw. The drop in Mw can be even higher for PLLA when sterilized with higher dose. The dose used is relatively low compared to that conventionally used to sterilize medical devices in order to minimize the molecular weight reduction.

A minimum molecular weight range for a final stent product after sterilization for satisfactory stent performance is preferred to be at least 120 kg/mol, in terms of Mw. Below this range a stent may degrade too fast and lose the radial strength sufficient to support a vessel lumen.

Due to the importance of the magnitude of the molecular weight, it is desirable to minimize or reduce the molecular weight drop that occurs during processing, in particular during sterilization and melt processing. The present invention includes the use of a polymer formulation that has an increased resistance to molecular weight reduction.

As indicated above, embodiments of the present invention include a stent scaffolding made from a polymer formulation that contains PLLA and polymandelide, or PLLA chemically modified with polymandelide. The polymandelide stabilizes the polymer formulation by reducing the amount of molecular weight degradation upon exposure to radiation and high temperatures.

Polymandelide (PM) is an aryl analogue of PLLA and can be synthesized by the ring-opening polymerization of mandelide, the cyclic dimer of mandelic acid. Liu, T., et al., Macromolecules, 2007, 40 (17), pp 6040-6047. As shown by the structure of polymandelide below, it differs from PLLA in that the methyl groups of the monomer units are replaced with phenyl groups.

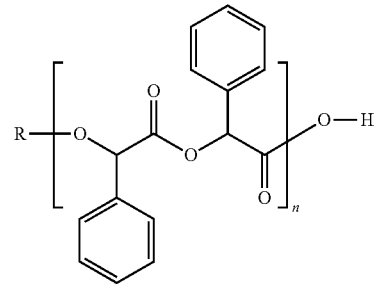

Polymandelide is a glassy amorphous polymer with a Tg of 100° C., with rheological properties comparable to polystyrene. Thermal gravimetric analyses under nitrogen show that the polymer is stable to 300° C. Liu, T., et al., Macromolecules, 2007, 40 (17), pp 6040-6047. Degradation of polymandelide in pH 7.4 buffer at 55° C. is consistent with a bulk erosion model and, due to its high Tg, proceeds at 1/100 the rate of PLLA under similar conditions. Liu, T., et al., Macromolecules, 2007, 40 (17), pp 6040-6047. The higher radiation and thermal stability of PLLA in the polymer formulation is due to the phenyl groups.

Polymandelide is more brittle at body temperature than PLLA. It is important for a polymeric stent body to have high fracture toughness since brittle behavior can result in fractures and premature failure of a stent. Additionally, polymandelide can reduce crystallinity of PLLA which may reduce strength. Also, the polymandelide can decrease the in vivo degradation rate of PLLA. Therefore, it is critical that a polymer formulation contain enough polymandelide to increase the radiation and thermal stability without adversely effecting stent performance, i.e., fracture toughness, strength, and in vivo degradation rate.

In some embodiments, the stent body can be made from a polymer formulation that is a blend of PLLA and polymandelide. In such embodiments, the polymer formulation includes less than 5 wt % of polymandelide. The blend can be made by mixing the PLLA and polymandelide in an extruder.

In a preferred embodiment, the polymer formulation contains between 2-5 wt % polymandelide. An amount of polymandelide greater than 5 wt % is likely to adversely affect the fracture toughness, strength, and degradation rate of the stent body. The Mw of the polymandelide in the blend can be 50-500 kg/mol and the Mw of the PLLA in the blend can be 300-600 kg/mol.

The polymandelide in the blend will increase the radiation and thermal stability of the PLLA in the blend. The polymandelide reduces the drop in molecular weight in the PLLA in the blend compared to PLLA without the polymandelide caused by exposure to a dose of radiation or processing at high temperature. The polymer formulation can be exposed to a higher dose of radiation than the PLLA without the polymandelide and still have a drop in molecular weight in the PLLA in the blend that is less than PLLA without the polymandelide.

In other embodiments, the stent body can be made from a polymer formulation that includes a poly(L-lactide-co-mandelide) random copolymer, poly(L-lactide-co-glycolide-co-mandelide) random copolymer, or poly(L-lactide-co-mandelide-caprolactone) random copolymer. In some of these embodiments, the copolymer includes only LLA and mandelide segments to improve the radiation and thermal stability of PLLA. In some of these embodiments, the polymer formulation contains LLA, mandelide and glycolide segments to further increase the degradation rate of the final product. In some of these embodiments, the polymer formulation contains LLA, mandelide and caprolactone segments to further increase the fracture resistance of the final product. The Mw of such random copolymer can be 300-600 kg/mol. The amount of mandelide segment should be less than 5 wt %. In the case that glycolide or caprolactone is used, glycolide content can be 5-20% and caprolactone content should be less than 5 wt %. Such random copolymers can be formed through ring opening polymerization by adding LLA and mandelide and other monomers such as glycolide or caprolactone together into the reactor.

In other embodiments, the stent body can be made from a polymer formulation that includes a block copolymer of PLLA and polymandelide. In some of these embodiments, the block copolymer includes only PLLA and polymandelide blocks. In some of these embodiments, the polymer formulation contains the block copolymer and PLLA with no polymandelide blocks. The block copolymer can be a linear block copolymer, such as a diblock or triblock copolymer. The triblock copolymer can have a middle block of PLLA and end blocks polymandelide. The Mw of the polymandelide blocks should be 10 kg/mol or less to avoid adverse effects on the stent properties and the Mw of the PLLA blocks can be 300-600 kg/mol.

The block copolymer has less than 5 wt % of polymandelide blocks. In a preferred embodiment, the block copolymer contains between 2-5 wt % polymandelide blocks. An amount of polymandelide blocks greater than 5 wt % can adversely affect the fracture toughness, strength, and degradation rate of the stent body.

The block copolymer can be formed by ring opening polymerization of L-lactide and mandelide by adding monomers in different sequences.

The increased radiation and thermal stability of the polymer formulation allows for greater flexibility in processing, in particular in radiation sterilization of the stent. In one set of embodiments, the radiation dose range for a radiation sterilization of the stent with a stent body made from the polymer formulation can be same range, 20-30 kGy, used for a PLLA stent body without polymandelide. In these embodiments, the molecular weight drop of the PLLA due to the radiation exposure will be less than a PLLA stent body without polymandelide.

In these embodiments, the radiation sterilization of the stent includes exposing the stent to a radiation dose between 20-30 kGy. As indicated above, the molecular weight drop from sterilization with this dose range resulted is about a 53% drop in Mw. Therefore, the drop in Mw of the polymer formulation stent body will be less than 53%. It is expected that the drop will be less than 30%, or even less than 20%. The amount of the drop varies with the amount of polymandelide in the blend or in the block copolymer.

As indicated above, the overall drop in Mw from extrusion to sterilization was about 70% for the PLLA stent without polymandelide. Since the polymer formulation also has greater thermal stability, the drop in Mw for extrusion, radial expansion, and blow molding will also be reduced. Therefore, the overall drop in Mw from extrusion to sterilization will be substantially less than 70%, for example, less than 50%, or even less than 30%.

In general, from a manufacturing standpoint, the radiation sterilization process is more efficient at an average radiation dose greater than 30 kGy, in particular, in a dose range of 25-50 kGy. This range allows the medical device to be manufactured without expensive manufacturing controls to reduce bioburden such that the higher low end tolerance is supported. The higher top end of the dose range allows for product to be processed in efficient load configurations to improve process throughput. In another set of embodiments, the radiation dose range for radiation sterilization of the stent with a stent body made from the polymer formulation can be higher than 30 kGy. The dose above 30 kGy can be adjusted so that the Mw of the PLLA of the polymer formulation of the irradiated stent body is at least 120 kg/mol, a minimum acceptable Mw preferred for PLLA stent application. The dose and polymandelide content can be adjusted so that the Mw is between the Mw resulting from a 20-30 kGy dose and a minimum acceptable Mw.

In one such embodiment, the preferred dose range is 25-50 kGy to provide efficiency in the sterilization process. The dose and polymandelide content can be adjusted to obtain a Mw of the PLLA of the polymer formulation that is above a minimum acceptable range of Mw. Alternatively, the drop in molecular weight due to radiation exposure is less than 50%.

In this second set of embodiments with the higher dose range, it is not desirable to use polymandelide alone to obtain the same drop in molecular weight as the lower dose range, 20-30 kGy. To achieve this, it would be necessary to increase the polymandelide content to a level that would adversely affect the performance of the stent.

In the third set of embodiments, the polymer formulation with polymandelide is used in combination with one or more additional stabilizing agents to further minimize or reduce the molecular weight reduction from radiation exposure. In this set of embodiments, the radiation dose for sterilization is higher than 30 kGy, with a preferred dose range of 25-50 kGy to provide efficiency in the sterilization process. The additional stabilizing agents further minimize or reduce the degradation in molecular weight.

In these embodiments, the reduction in molecular weight can be in the same range as that obtained in the first set of embodiments that uses a dose in the range of 20-30 kGy. For instance, the drop in Mw will be less than 30%, or even less than 20%. The types and amount of additional stabilizing agents can be adjusted to control the reduction in molecular weight. In this set of embodiments, the molecular weight degradation is reduced (e.g., to the level of the first set of embodiments), but a more efficient sterilization process is also obtained because of the high dose range as compared to sterilization of PLLA at 20-30 kGy without polymandelide (or any other stabilizing agent or method).

The one or more stabilizing agents can include, but are not limited to, oxygen scavengers or absorbers, desiccants to remove moisture, and free radical scavengers. As indicated above, oxygen, moisture, and free radicals generated by irradiation all contribute to reduction in molecular weight.

"Free radicals" refer to atomic or molecular species with unpaired electrons on an otherwise open shell configuration. A free radical scavenger effectively competes with the polymer for the free radicals, and thus removes the free radicals from the reaction cycle, thus reducing the molecular weight reduction caused by free radicals.

A desiccant is a scavenger for moisture and is also referred to as a drying agent, moisture absorber, etc. A desiccant is a substance that is hygroscopic or that absorbs water from the surrounding environment.

Oxygen scavengers may include those compounds capable of absorbing oxygen, as well as reactive materials that may consume oxygen through chemical reaction. Typically, those capable of absorbing oxygen are inorganic in nature, while those which consume oxygen through chemical reaction are organic reactive materials.

The one or more stabilizing agents may be used to reduce molecular weight reduction of the polymer formulation of the stent body by incorporating the agents in the scaffolding or disposing the agents within a package, adjacent to the stent body, that encloses the stent during sterilization. The agents can also be incorporated in the stent body and disposed within the sealed package.

The stent body or scaffolding can include one or more of the stabilizing agents mixed dispersed into the polymer formulation of the stent body. These stabilizing agents, which may be in a particulate form, may be incorporated into the stent body by melt processing. For example, the agents may be mixed into the polymer formulation during an extrusion process which may be the extrusion process which forms the stent precursor tube.

The polymer formulation of the stent body can include between 0.1-2% wt % of stabilizing agents, which refers to the total weight percent of all stabilizing agents. The polymer formulation may contain the same weight percent of all types of stabilizing agents or different weight percent of each. The total amount of stabilizing agent should be limited to the range provided since an amount much above this is expected to adversely affect mechanical properties of the stent body.

In some embodiments, one more stabilizing agents may be incorporated in the stent body and one or more different agents may be disposed in the package. For example, free radical scavengers can be incorporated in the stent body and desiccants or oxygen scavengers or both desiccants and oxygen scavengers are disposed in the package. This alternative can be an advantage since the adverse effect of stabilizers on the properties of the stent body is reduced by having stabilizers in the package.

Some representative examples of free radical scavengers include, without limitation, BHT, BHA, trihydroxybutyrophenone, L-ascorbic acid, (Vitamin C), sodium ascorbate, Vitamin E, herbal rosemary, sage extracts, glutathione, melatonin, carotenes, carotenoids, resveratrol, methyl gallate, n-octyl gallate, n-dodecyl gallate, propyl gallate, propyl paraben, luteolin, eriodictyol, astaxanthin, anthocyanins, carnosol, quercetin, catechin, morin, rutin, boldine, tocopherols, hydroxytyrosol, ubiquinol, isoflavones, lycopene, fisetin, ellagic acid, L-DOPA, sinapine, olivetol, dehydrozingerone, curcumin, and tertbutylhydroquinone. Other free radical scavengers, such as various isomers of Vitamin E, may be used, including the four tocopherols and four tocotrienols. The alpha, beta, gamma and delta forms of both the tocopherols and tocotrienols may be used to prevent chemical degradation.

Examples of suitable desiccants or moisture scavengers include, but are not limited to, silica gel, anhydrous calcium sulfate (anhydrite), calcium sulfate dihydrate (gypsum), calcium oxide, montmorillonite clay, molecular sieves such as those including natural or synthetic zeolite, activated alumina, para-toluene sulfonyl isocyanate, molecular sieves, oxazolidine, etc. Anhydrous calcium sulfate is available from GypsumSolutions.com, The Industrial Products Division of United States Gypsum Company in Chicago, Ill., one example of which is CA-5 having an average particle size of about 1.4 microns.

Examples of inorganic oxygen scavengers include, but are not limited to, sulfites such as potassium sulfite, bisulfites, etc. Examples of organic oxygen scavengers include, but are not limited to unsaturated hydrocarbons, ascorbic acid and its derivatives (including its alkali metal salts, optical isomers and derivatives thereof), and ascorbate compounds. Unsaturated hydrocarbons include, but are not limited to diene polymers such as polyisoprene, polybutadiene (especially 1,2-polybutadienes, which are defined as those polybutadienes possessing greater than or equal to 50% 1,2 microstructure), and copolymers thereof, e.g. styrene-butadiene. Such hydrocarbons also include polymeric compounds such as polypentenamer, polyoctenamer, and other polymers prepared by olefin metathesis; diene oligomers such as squalene; and polymers or copolymers derived from dicyclopentadiene, norbornadiene, 5-ethylidene-2-norbornene, or other monomers containing more than one carbon-carbon double bond (conjugated or non-conjugated). These hydrocarbons further include carotenoids such as β-carotene.

In further embodiments, a crosslinking agent can be incorporated into the scaffolding as an alternative to a one or more stabilizing agents or in addition to stabilizing agents. The crosslinking agent is capable of inducing crosslinking of the polymer formulation upon exposure to radiation. The crosslinking reduces the molecular weight degradation during sterilization.

In such embodiments, the polymer formulation can be crosslinked by exposure to radiation prior to the sterilization step or during the sterilization step. In particular, the polymer formulation can be crosslinked after radial expansion and prior to laser machining or after laser machining and prior to crimping.

Exemplary crosslinking agents include triallyl isocyanurate (TAIC), trimethally isocyanurate (TMAIC), and trimethylolpropane triacrylate (TMPTA), however, other crosslinking agents may be used. The radiation dose can be 10-100 kGy, 30-40 kGy, or more narrowly 20-30 kGy. It has been found that TAIC is the most effective crosslinking agent in PLLA since it exhibits the highest crosslink density at the lowest dose at 3 wt % for each crosslinking agent. Mitomo, Hiroshi et al., Polymer 46 4695-4703 (2005).

A crosslinking agent can be mixed or dispersed into the bioabsorbable polymer of a tube using melt processing. For example, the crosslinking agent can be fed into an extruder that in the manufacture of the tube. Alternatively, the crosslinking agent can be mixed with a polymer melt in batch and fed into a extruder or injection molder to make the tube.

In additional embodiments, in addition to the use of polymandelide and stabilizing agents, the stent can be sterilized with an average e-beam dose to as low as 17.5 kGy with a tight dose range of ±2 kGy. In such embodiments, the processing will include better bioburden control so that the bioburden of stent prior to processing will have a lower bioburden and/or use of alternative sterilization validation models.

For the purposes of the present invention, the following terms and definitions apply:

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility.

EXAMPLE

Step 1 (tubing preparation): 950 g PLLA, 50 g polymandelide and 2 g vitamin E are mixed together and then extruded into tubing with OD at 0.64" and ID at 0.21".

Step 2 (stent preparation): prepare stent through tubing expansion (ID=0.124" and OD=0.136"), femto second laser cutting, stent coating and crimping (down to OD=0.53)".

Step 3 (e-beam sterilization): put stents into an aluminum pouch containing a small packet of oxygen and moisture absorber in it, then seal the pouch with argon pouch sealer. The stent would be sterilized at 25 kGy with a dosage range from 22.5 to 30 kGy.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent comprising a stent scaffolding, the stent scaffolding including a polymer formulation including poly(L-lactide) and polymandelide.

2. The stent of claim 1, wherein the scaffolding comprises 2-5 wt % of the polymandelide.

3. The stent of claim 1, wherein the polymer formulation comprises a blend of poly(L-lactide) and the polymandelide.

4. The stent of claim 3, wherein the poly(L-lactide) has a weight average molecular weight of 300-600 kg/mol and the polymandelide has a weight average molecular weight of 50-500 kg/mol.

5. The stent of claim 3, wherein the scaffolding comprises 2-5 wt % of the polymandelide.

6. The stent of claim 1, wherein the polymer formulation comprises a block copolymer of the poly(L-lactide) and the polymandelide.

7. The stent of claim 6, wherein the poly(L-lactide) has a weight average molecular weight of 50-500 kg/mol and the polymandelide has a weight average molecular weight less than 10 kg/mol.

8. The stent of claim 6, wherein the polymandelide blocks are 2-5 wt % of the polymer formulation.

9. A stent comprising a stent scaffolding, the stent scaffolding including a polymer formulation that includes a random copolymer formed from monomers comprising L-lactide and mandelide.

10. The stent of claim 9, wherein the random copolymer is poly(L-lactide-co-mandelide).

11. The stent of claim 9, wherein the monomers further comprise caprolactone, glycolide, or both.

12. The stent of claim 9, wherein the random copolymer has a weight average molecular weight of 300-600 kg/mol.

13. The stent of claim 1, wherein the polymer formulation is crosslinked.

14. The stent of claim 1, wherein the stent is crimped over a balloon.

15. A stent comprising a stent scaffolding, the stent scaffolding comprising:
a polymer formulation including poly(L-lactide) and polymandelide; and
one or more stabilizing agents incorporated in the scaffolding, wherein the one or more stabilizing agents reduce the molecular weight reduction of the poly(L-lactide) upon its exposure to radiation, wherein the stabilizing agents are selected from the group consisting of a free radical scavenger, an oxygen scavenger, and a dessicant.

16. The stent of claim 15, wherein the one or more stabilizing agents are dispersed in the polymer formulation of the scaffolding.

17. The stent of claim 15, wherein the scaffolding comprises 0.1 to 2 wt % of the stabilizing agents.

18. The stent of claim 15, wherein the polymer formulation comprises a blend of poly(L-lactide) and the polymandelide.

19. The stent of claim 18, wherein the scaffolding comprises 2 to 5 wt % of the polymandelide.

20. The stent of claim 15, wherein the polymer formulation comprises a block copolymer of the poly(L-lactide) and the polymandelide.

21. The stent of claim 20, wherein the polymandelide blocks are 2 to 5 wt % of the stent scaffolding.

22. A stent comprising a stent scaffolding, the stent scaffolding comprising:
a polymer formulation including a random copolymer formed from monomers comprising L-lactide and mandelide; and
one or more stabilizing agents incorporated in the scaffolding, wherein the one or more stabilizing agents reduce the molecular weight reduction of the random copolymer upon its exposure to radiation, wherein the stabilizing agents are selected from the group consisting of a free radical scavenger, an oxygen scavenger, and a dessicant.

23. A medical device system comprising:
a sealed package;
a stent scaffolding disposed within the sealed package, wherein the scaffolding comprises a polymer formulation including poly(L-lactide) and polymandelide; and
one or more stabilizing agents within the sealed package, wherein the one or more stabilizing agents reduce the molecular weight reduction of the poly(L-lactide) upon its exposure to radiation, wherein the stabilizing agents are selected from the group consisting of a free radical scavenger, an oxygen scavenger, and a dessicant.

24. The system of claim 23, wherein one or more of the stabilizing agents are incorporated in the scaffolding and the scaffolding comprises 0.1 to 2 wt % of the stabilizing agents incorporated in the scaffolding.

25. The system of claim 24, wherein the stabilizing agents incorporated in the scaffolding are dispersed in the polymer formulation of the scaffolding.

26. The system of claim 23, wherein the free radical scavenger is incorporated in the scaffolding and the dessicant, the oxygen scavenger, or both are disposed adjacent to the stent scaffolding within the package.

27. The system of claim 23, wherein the dessicant, the oxygen scavenger, or both is disposed adjacent to the stent scaffolding within the sealed package.

* * * * *